(12) United States Patent
Kushmaro et al.

(10) Patent No.: US 8,158,401 B2
(45) Date of Patent: Apr. 17, 2012

(54) METHOD FOR ISOLATING AND CULTURING UNCULTURABLE MICROORGANISMS

(75) Inventors: Ariel Kushmaro, Moshav Nir-Zvi (IL); Shimona Geresh, Omer (IL); Shaul Geresh, legal representative, Omer (IL)

(73) Assignee: Ben-Gurion University of the Negev Research and Development Authority, Beer Sheva (IL)

( * ) Notice: Subject to any disclaimer, the term of this patent is extended or adjusted under 35 U.S.C. 154(b) by 0 days.

(21) Appl. No.: 12/537,646

(22) Filed: Aug. 7, 2009

(65) Prior Publication Data

US 2010/0120037 A1 May 13, 2010

Related U.S. Application Data

(63) Continuation of application No. 10/527,076, filed as application No. PCT/IL03/00725 on Sep. 3, 2003, now abandoned.

(51) Int. Cl.
*C12Q 1/68* (2006.01)
*C12N 1/00* (2006.01)
*C12N 1/02* (2006.01)
*C12N 1/06* (2006.01)
*C12N 1/20* (2006.01)
*C12N 3/00* (2006.01)

(52) U.S. Cl. .................. 435/243; 435/6.15; 435/252.1; 435/242

(58) Field of Classification Search .............. 435/6.15, 435/242, 243, 252.1
See application file for complete search history.

(56) References Cited

U.S. PATENT DOCUMENTS

| 4,649,109 A | 3/1987 | Perlman |
| 5,032,508 A | 7/1991 | Naughton et al. |
| 5,744,325 A | 4/1998 | Fujishima et al. |
| 2003/0059866 A1 | 3/2003 | Lewis et al. |
| 2003/0059867 A1 | 3/2003 | Lewis et al. |

FOREIGN PATENT DOCUMENTS

WO 2005010169 A1 2/2005

OTHER PUBLICATIONS

McCormick , D. 1986. Detection Technology: The Key to Environmental Biotechnology. Bio/Technology, vol. 4, pp. 419, 421-422.*
Weaver, J.C. 1990. Sampling :a critical problem in biosensing.Med. & Biol. Eng. & Comput., vol. 28, pp. B3-B9.*
Weaver et al. 1991.Microdrop Technology: A General Method for Separating Cells by Function and Composition. Methods: A Companion to Methods In Enzymology, vol. 2. No. 3, pp. 234-247.*
Manome, A. et al. 2001. Application of gel microdroplet and flow cytometry techniques to selective enrichment of non-growing bacterial cells. FEMS Microbiology Letters, vol. 197, pp. 29-33.*
T. Kaeberlein et al., "Osilating "Uncultivable" Microorganisms in Pure Culture in a Simulated natural Environment", Science, vol. 296, pp. 1127-1129, May 10, 2002.
Zengler K. et al., "Cultivating the uncultured", PNAS, vol. 99. No. 24. pp. 15681-15686 (Nov. 26, 2002).

* cited by examiner

*Primary Examiner* — Jon P Weber
*Assistant Examiner* — Kailash C Srivastava
(74) *Attorney, Agent, or Firm* — Browdy and Neimark, PLLC

(57) ABSTRACT

The invention provides a method for isolating and culturing a previously unculturable microorganism, which comprises: (i) collecting a sample from an environmental source; (ii) counting/estimating the number of microorganisms in the sample; (iii) diluting the sample in an appropriate medium; (iv) adding a gelating agent such as to entrap one or more microorganisms within a sphere of the gelating agent; (v) coating the spheres containing the entrapped microorganism(s) with a natural or synthetic polymer to form a polymeric membrane; (vi) incubating the coated spheres in the original environment for an appropriate time; (vii) cutting the spheres and scanning for microorganisms colonies; and (viii) isolating the microorganisms, and repeating steps (iii) to (vii) until a pure clone of said previously unculturable microorganism is obtained.

9 Claims, 2 Drawing Sheets

SEQUENCE LISTING

<160> NUMBER OF SEQ ID NOS: 9

<210> SEQ ID NO 1
<211> LENGTH: 26
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (17)..(18)
<223> OTHER INFORMATION: y (residue 17) is c or t, m (residue 18) is a
      or c

<400> SEQUENCE: 1
ggatccagac tttgatymtg gctcag                                          26

<210> SEQ ID NO 2
<211> LENGTH: 30
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (14)..(14)
<223> OTHER INFORMATION: y (residue 14) is c or t

<400> SEQUENCE: 2
gtgaagctta cggytagctt gttacgactt                                      30

<210> SEQ ID NO 3
<211> LENGTH: 1428
<212> TYPE: DNA
<213> ORGANISM: Artificial Sequence
<220> FEATURE:
<223> OTHER INFORMATION: Synthetic

<400> SEQUENCE: 3
agtcgaacgg cagcgcgaga gagcttgctt ttttggcggc gagtggcgga cgggtgagta      60
atatatcgga acgtgcccag tagcggggga taactactcg aaagagtggc taataccgca     120
tacgccctac gggggaaagg gggggatcgc aagacctctc actattggag cggccgatat     180
cggattagct agttggtggg gtaaaggctc accaaggcaa cgatccgtag ctggtttgag     240
aggacgacca gccacactgg gactgagaca cggcccagac tcctacggga ggcagcagtg     300
gggaattttg gacaatgggg gaaaccctga tccagccatc ccgcgtgtat gatgaaggcc     360
ttcgggttgt aaagtacttt tggcagagaa gaaaaggtat cccctaatac gggatactgc     420
tgacggtatc tgcagaataa gcaccggcta actacgtgcc agcagccgcg gtaatacgta     480
gggtgcaagc gttaatcgga attactgggc gtaaagcgtg tgtaggcggt tcggaaagaa     540
agatgtgaaa tcccaggggc tcaaccttgg aactgcattt taactgccg agctagta       600 tgtcagaggg gggtagccat tccacgtgta gcagtgaaat gcgtagatat gtggaggaat     660
accgatggcg aaggccgccc cctgggataa tactgacgct cagacacgaa agcgtgggga     720
gcaaacagga ttagataccc tggtagtcca cgccctaaac gatgtcaact agctgttggg     780
gccgttaggc cttagtagcg cagctaacgc gtgaagttga ccgcctgggg agtacggtcg     840
caagattaaa actcaaagga attgacgggg acccgcacaa gcggtggatg atgtggatta     900
attcgatgca acgcgaaaaa ccttacctac ccttgacatg tctggaaagc cgaagagatt     960
tggccgtgct cgcaagagaa ccggaacaca ggtgctgcat ggctgtcgtc agctcgtgtc    1020

```
gtgagatgtt gggttaagtc ccgcaacgag cgcaacccct gtcattagtt gctacgcaag    1080
agcactctaa tgagactgcc ggtgacaaac cggaggaagg tggggatgac gtcaagtcct    1140
catggccctt atgggtaggg cttcacacgt catacaatgg tcgggacaga gggtcgccaa    1200
cccgcgaggg ggagccaatc tcagaaaccc gatcgtagtc cggatcgcag tctgcaactc    1260
gactgcgtga agtcggaatc gctagtaatc gcggatcaga atgtcgcggt gaatacgttc    1320
ccgggtcttg tacacaccgc ccgtcacacc atgggagtgg gtttcaccag aagtaggtag    1380
cctaaccgta aggagggcgc ttaccacggt gggaatcatg actgggag                1428

<210> SEQ ID NO 4
<211> LENGTH: 1382
<212> TYPE: DNA
<213> ORGANISM: Artificial Sequence
<220> FEATURE:
<223> OTHER INFORMATION: Synthetic

<400> SEQUENCE: 4
gaagaccgct ggcggcaggc ctagcacatg caagtcgagc gcaccttcgg gtgagcggcg      60
gacgggttag taacgcgtgg gaacgtaccc agatctgcgg aatagccact ggaaacggtg     120
agtaataccg catacgccct tcgggggaaa gatttatcgg atttggatcg gcccgcgtta     180
gattagatag ttggtgggt aatggcctac caagtctacg atctatagct ggttttagag      240
gatgatcagc aacactggga ctgagacacg gcccagactc ctacgggagg cagcagtggg     300
gaatcttgga caatgggcgc aagcctgatc agccatgccg cgtgagtga tgaaggccct      360 agggtcgtaa agctctttcg ccagggaaga taatgacggt acctggtaaa gaaaccccgg     420
ctaactccgt gccagcagcc gcggtaatac ggaggggtt agcgttgttc ggaattactg      480
ggcgtaaagc gcgcgtaggc ggactattaa gtcgagggtg aaatcccggg gctcaacccc     540
ggaactgcct tcgatactgg tagtcttgag gtcgagagag gtgagtggaa ctccgagtgt     600
agaggtgaaa ttcgtagata ttcggaagaa caccagtggc gaaggcggct cactggctcg     660
atactgacgc tgaggtgcga aagtgtgggg agcaaacagg attagatacc ctggtagtcc     720
acaccgtaaa cgatgaatgc cagtcgtcgg gtagcatgct attcggtgac acacctaacg     780
gattaagcat tccgcctggg gagtacggtc gcaagattaa aactcaaagg aattgacggg     840
ggcccgcaca agcggtggag catgtggttt aattcgaagc aacgcgcaga accttaccaa     900
cccttgacat cccgtgaccg ctggagagat ccagtttccc ttcggggcac ggtgacaggt     960
gctgcatggc tgtcgtcagc tcgtgtcgtg agatgttcgg ttaagtccgg caacgagcgc    1020
aactcacacc cttagttgcc agcctttagt gggcactcta ggggaactgc ccgtgataag    1080
cgggaggaag gtgtggatga cgtcaagtcc tcatggccct tacgggttgg gctacacacg    1140
tgctacaatg gcatctacag tgggttaatc ccaaaaagat gtctcagttc ggattgtcgt    1200
ctgcaactcg acggcatgaa gtcggaatcg ctagtaatcg cgtaacagca tgacgcggtg    1260
aatacgttcc cgggccttgt acacaccgcc cgtcacacca tgggagttgg gtctacccga    1320
aggccgtgcg ctaactttg aggcagcggg gccacggtag gctcagcgag tggggtgtcc    1380
cc                                                                  1382

<210> SEQ ID NO 5
<211> LENGTH: 1483
<212> TYPE: DNA
<213> ORGANISM: Artificial Sequence
<220> FEATURE:
<223> OTHER INFORMATION: Synthetic
```

<400> SEQUENCE: 5

```
tgacgctggc ggcgtggttc agactccaag tcgaacggga ctctttaact agcttgctat    60
ttaaagatga gagtggcgaa cgggtgcgta acacgtaaag aacctaccct tatgtctggg   120
atagcccacc gaaaggtgga ttaataccgg atgtgatctc tcttctcatg aagagaatat   180
taaagctggg gaccttcggg cctggcgcat aaggagggct tgcggccta tcagcttgtt    240
ggtgaggtaa cggctcacca aggctaagac gggtagctgg tctgagagga tgatcagcca   300
cactggaact tagacacggt ccagacacct acggtggca gcagtttcga atctttcaca    360
atgggcgaaa gcctgatgga gcaacgccgc gtggggatg aaggccttcg ggttgtaaac    420
ccctgtcacc aaggataaaa cgctatctat aatactagg tagcctgatg taacttggag    480
aggaaggagt ggctaactct gtgccagcag ccgcggtaat acagagactc caggcgttat   540
tcggattcac tgggcgtaaa gggtgcgcag gcggtcagat gtgtcaggtg tgaaatactg   600
cagcttaact gtagaactgc acttgaaact atttgactag agtatcggag aggtaagcgg   660
aattccaggt gtagcagtga aatgcgtaga tatctggagg aacaccaatg gcgaaggcag   720
cttactggac gattactgac gctcaggcac gaaagcatgg ggagcgaaag ggattagata   780
cccctgtagt ccatgccgta acgttgttc actaactgtt ggaggattcg acccccttcag   840
cggccaagct aacgcgataa gtgaaccgcc tgaggactac ggccgcaagg ctaaaactca    900
aaggaattga cggggcctg cacaagcggt ggagcatgtg cttaattcg atgcaacgcg     960
aagaacctta cctaggcttg acatgtggac daccggggca gagatgccct ttctcttcgg  1020
agcggctaca caggtgctgc atggctgtcg tcagctcgtg tcgtgagatg tttggttaag  1080
tccagcaacg agcgcaaccc ctgccactag ttgccagcat ttagttgggg actctagtgg  1140
gacaaactct ctctgagagt gggaaggtgg ggacgacgtc aagtcagtat ggcccttacg  1200
tctagggctg cacacgtgct acaatgcccg gtacagaggg acgcaatacc gcgaggtgga  1260
gcaaatcctt aaagccgggc ccagttcaga ttggagtctg caactcgact ccatgaagtt  1320
ggaatcgcta gtaatggcgc atcagctacg gcgccgtgaa tacgttccca ggccttgtac  1380
acaccgcccg tcacgttatg gaagcccggt cttgccccga agtatgttag ctaacccctt  1440
gtgggtggcg atgtcctaag gtgaggctgg taactggaac gaa                    1483
```

<210> SEQ ID NO 6
<211> LENGTH: 730
<212> TYPE: DNA
<213> ORGANISM: Artificial Sequence
<220> FEATURE:
<223> OTHER INFORMATION: Synthetic

<400> SEQUENCE: 6

```
atgccacgct agcgggatgc tttacacatg caagtcgaac ggcagcgcga gagagcttgc    60
tctcttggcg gcgagtggcg gacgggtgag taatatatcg gaacgtgccc agtagcgggg   120
gataactact cgaaagagtg gctaataccg catacgccct acgggggaaa gggggggatc   180
gcaagacctc tcactattgg agcggccgat atcggattag ctagttggtg ggtaaaggc    240
tcaccaaggc aacgatccgt agctggtttg agaggacgac cagccacact gggactgaga   300
cacggcccag actcctacgg gaggcagcag tgggaatttt ggacaatggg ggaaaccct    360
gatccagcca tcccgcgtgt atgatgaagg ccttcgggtt gtaaagtact tttggcagag   420
aagaaaaggt atcccctaat acgggatact gctgacggta tctgcagaat aagcaccggc   480
taactacgtg ccagcagccg cggtaatacg tagggtgcaa gcgttaatcg gaattactgg   540
```

```
gcgtaaagcg tgtgtaggcg gttcggaaag aaagatgtga atcccaggg  ctcaaccttg        600 gaactgcatt tttaactgcc gagctagagt atgtcagagg ggggtagaat tccacgtgta        660
gcagtgagat gcgtagatat gtggaggaat accgatggcg aagcagcccc ctgggatata        720
ctgacgctca                                                               730

<210> SEQ ID NO 7
<211> LENGTH: 689
<212> TYPE: DNA
<213> ORGANISM: Artificial Sequence
<220> FEATURE:
<223> OTHER INFORMATION: Synthetic

<400> SEQUENCE: 7
cccccagtct gattcccacc gtggtaagcg ccctccttac ggttaggcta cctacttctg         60
gtgaaaccca ctcccatggt gtgacgggcg gtgtgtacaa gacccgggaa cgtattcacc        120
gcgacattct gatccgcgat tactagcgat tccgacttca cgcagtcgag ttgcagactg        180
cgatccggac tacgatcggg tttctgagat tggctccccc tcgcgggttg gcgaccctct        240
gtcccgacca ttgtatgacg tgtgaagccc tacccataag ggccatgagg acttgacgcc        300
atccccacct cctccggtt  tgtcaccggc agtctcatta gagtgctctt gcgtagcaac        360
taatgacaag ggttgcgctc gttgcgggac ttaacccaac atctcacgac acgagctgac        420
gacagccatg cagcacctgt gttccggctc tcttgcgagc acggccaaat ctcttcggct        480
ttccagatat gtcaagggta ggtaaggttt ttcgcgttgc atcgaattaa tccacatcat        540
ccaccgcttg tgcgggtccc cgtcaattcc tttgagtttt aatcttgcga ccgtactccc        600
caggcggtca acttcacgcg ttagctgcgc tactaaggcc taacggcccc aacagctagt        660
tgacatcgtt tagggcgtgg actaccagg                                         689

<210> SEQ ID NO 8
<211> LENGTH: 651
<212> TYPE: DNA
<213> ORGANISM: Artificial Sequence
<220> FEATURE:
<223> OTHER INFORMATION: Synthetic

<400> SEQUENCE: 8
ggatgaacgc tggcggcagg cctaacacat gcaagtcgag cggtagagag aagcttgctt         60
ctcttgagag cggcggacgg gtgagtaatg cctaggaatc tgcctggtag tgggggataa        120
cgttcggaaa cggacgctaa taccgcatac gtcctacggg agaaagcagg ggaccttcgg        180
gccttgcgct atcagatgag cctaggtcgg attagctagt tggtggggta atggctcacc        240
aaggcgacga tccgtaactg gtctgagagg atgatcagtc acactggaac tgagacacgg        300
tccagactcc tacggaggc  agcagtgggg aatattggac aatgggcgaa agcctgatcc        360
agccatgccg cgtgtgtgaa gaaggtcttc ggattgtaaa gcactttaag ttgggaggaa        420
gggttgtaga ttaatactct gcaattttga cgttaccgac agaataagca ccggctaact        480
ctgtgccagc agccgcggta atacagaggg tgcaagcgtt aatcggaatt actgggcgta        540
aagcgcgcgt aggtggttag ttaaagttgg gatgtgaaat ccccgggctc aaccctggga        600
actgcattca aaactgactg actagggtat ggtagagggt ggtggaattt c                651

<210> SEQ ID NO 9
<211> LENGTH: 686
<212> TYPE: DNA
<213> ORGANISM: Artificial Sequence
```

```
<220> FEATURE:
<223> OTHER INFORMATION: Synthetic

<400> SEQUENCE: 9
cccccagtca tgattacacc gtggtaaccg tcctcccgaa ggttagacta gctacttctg      60
gtgcaaccca ctcccatggt gtgacgggcg gtgtgtacaa ggcccgggaa cgtattcacc     120
gcgacattct gattcgcgat tactagcgat tccgacttca cgcagtcgag ttgcagactg     180
cgatccggac tacgatcggt tttgtgggat tagctccacc tcgcggcttg gcaaccctct     240
gtaccgacca ttgtagcacg tgtgtagccc aggccgtaag ggccatgatg acttgacgtc     300
atccccacct tcctccggtt tgtcaccggc agtctcctta gagtgccac cattacgtgc      360 tggtaactaa ggacaagggt tgcgctcgtt acgggactta acccaacatc tcacgacacg     420
agctgacgac agccatgcag cacctgtctc aatgttcccg aaggcaccaa tctatctcta     480
gaaagttcat tggatgtcaa ggcctggtaa ggttcttcgc gttgcttcga attaaaccac     540
atgctccacc gcttgtgcgg gccccgtca attcatttga gttttaacct tgcggccgta      600
ctccccaggc ggtcaactta atgcgttagc tgcgccacta agagctcaag gctcccaacg     660
gctagttgac atcgtttacg gcgtgg                                          686
```

METHOD FOR ISOLATING AND CULTURING UNCULTURABLE MICROORGANISMS

FIELD OF THE INVENTION

The present invention relates to a method for isolating and culturing novel "uncultivable" microorganisms.

BACKGROUND OF THE INVENTION

Cultured microorganisms are the most common source of antibiotics and other medicinal agents. However, only a small percentage (less than 1%) of the viable bacteria in soil can be cultured on known nutrient media using current techniques such as petri dishes (Handelsman et al. 1998; Amann et al. 1995). The other 99% of uncultured/uncultivable microorganisms, with their genetic and biochemical diversity, may emerge as a major source of new natural chemical structures that may be useful for humans, for example as drugs.

The exploration of previously uncultured microorganisms for the discovery of new useful natural products is now being carried out in several laboratories. The main approach involves genomics techniques such as the approach designated metagenomics for the analysis of the collective genomes of the microorganisms in the soil community. According to this approach, DNA in large segments is cloned directly from soil into a culturable host and a sequence-based and functional genomic analysis is conducted on it. The intention is the isolation of new signals, new secondary metabolites that might have utility for humans, and the reconstruction of an entire genome of an uncultured organism.

Molecular microbial ecology represents a recent development in research methods. It consists of utilizing techniques of molecular biology to investigate the ecology of microorganisms, and offers new tools to facilitate the detection and identification of microorganisms in the environment.

Molecular microbial ecology allowed the development of tools to address a central dogma of microbial ecology: an inability to cultivate more than a small proportion (0.1-1%) of the bacteria that can be visualized by direct count procedures (Head et al., 1998). Thus, the identification of bacteria by molecular methods represents an indispensable addition to the traditional methods based on the analyses of morphological and physiological characteristics. Among these culture-independent new techniques, the technique based on direct sequencing seems to be the most effective. It consists in sequencing a specific region of the bacterial chromosome, namely the bacterial 16S rDNA region, and in comparing this sequence with known sequences stored in data banks. All microorganisms possess at least one copy of the genes coding for the ribosomal RNA (rRNA), which are indispensable in any cells for the biosynthesis of proteins. Within these genes, the 16S rDNA region is principally used for the determination of the genus and the species of bacteria. By using this approach, it could be determined in many environmental samples the predominance of many different uncultured species. It might be feasible that the yet uncultured types of bacteria might be grown under laboratory conditions if just the right nutrients are found (Amann et al. 1995; Felske et al. 1999).

Recently, Kaeberlein et al. (2002, and published US Patent Applications Nos. 2003/0059866 and 2003/0059867) disclosed a new method for isolating and growing uncultivable microorganisms in pure culture in a simulated natural environment using a diffusion chamber. Microorganisms were separated from intertidal marine sediment particles, serially diluted, mixed with warm agar made with seawater, and placed in the diffusion chamber. The membranes allowed exchange of chemicals between the chamber and the environment, but restricted movement of cells. After the first membrane was affixed to the base of the chamber, the agar with microorganisms was poured in, and the top was sealed with another membrane (See FIG. 1, Kaeberlein et al., 2002' and FIG. 1a, US Patent Application No. 2003/0059866). The diffusion chamber consists of a stainless steel washer (70 mm o.d., 33 mm i.d., 3 mm in thickness) sandwiched between two 0.03-µm pore-size polycarbonate membranes. The membranes were glued to the washer forming the inner space filled with test microorganisms in semi-solid agar. The sealed chambers were placed on the surface of the sediment collected from the tidal flat and kept in a marine aquarium. Colonies of representative marine microorganisms were isolated in pure culture. These isolates did not grow on artificial media alone but formed colonies in the presence of other microorganisms.

Zengler et al. (2002) disclose a universal method that provides access to the immense reservoir of untapped microbial diversity. They utilized a technique that combines encapsulation of cells in gel microdroplets (using the OneCell System technology) for massively parallel microbial cultivation under low nutrient flux conditions, followed by flow cytometry to detect microdroplets containing microbial microcolonies.

In summary, most microorganisms in the environment have been overlooked as yet due to their resistance to cultivation on artificial media. The cultured microorganisms represent only a small fraction of natural microbial communities and hence the microbial diversity in terms of species richness and species abundance is grossly underestimated. Our understanding of microbial diversity is not represented by the cultured fraction of the microbial community (Wintzingerode et al., 1997).

SUMMARY OF THE INVENTION

It is an object of the present invention to provide a method for isolating and culturing previously unculturable microorganism.

In one preferred embodiment of the invention, the sample is collected from an environmental source and diluted in an appropriate medium after counting/estimating the number of microorganisms in the sample. A gelating agent is then added such as to entrap one or more microorganisms within a sphere of the gelating agent. The spheres containing the entrapped microorganism(s) are then coated with a natural or synthetic polymer to form a polymeric membrane. The coated spheres with the entrapped microorganisms are incubated in the original environment and, after an appropriate time, are cut and scanned for microorganisms colonies. The microorganisms are isolated and subjected one or more times to the steps of dilution in an appropriate medium, entrapping in a gelating agent, coating of the spheres containing the entrapped microorganisms, incubation of the coated spheres, cutting the spheres and scanning for microorganisms colonies, until a pure clone of said previously unculturable microorganism is obtained.

The present invention further provides a library of microorganisms obtained by the method of the invention, wherein each of the microorganisms was isolated from a sphere as described.

The present invention still further provides a method for screening and identification of new drugs and other substances of commercial interest in the pharmaceutical, chemical, biotechnology and other industries as well as in the agriculture, which comprises cultivating a previously unculturable microorganism or screening a library of previously unculturable microorganisms, and isolating and identifying compounds having biological or other activity of interest.

DETAILED DESCRIPTION OF THE INVENTION

Figure 1:
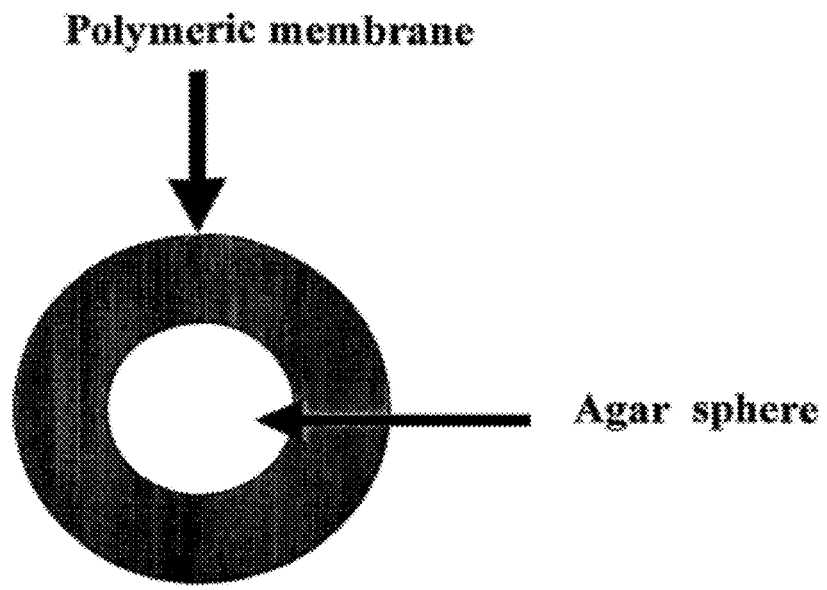
FIG. 1 depicts a schematic drawing of an agar sphere coated with a polymeric membrane.

The present invention relates to a method for isolation and culture of microorganisms suitable for microorganisms from any environmental source.

According to one aspect, the present invention relates to a method for isolating and culturing a previously unculturable microorganism, which comprises:
(i) collecting a sample from an environmental source;
(ii) counting/estimating the number of microorganisms in the sample;
(iii) diluting the sample in an appropriate medium;
(iv) adding a gelating agent such as to entrap one or more microorganisms within a sphere of the gelating agent;
(v) coating the spheres containing the entrapped microorganism(s) with a natural or synthetic polymer to form a polymeric membrane;
(vi) incubating the coated spheres in the original environment for an appropriate time;
(vii) cutting the spheres and scanning for microorganisms colonies; and
(viii) isolating the microorganisms, and repeating steps (iii) to (vii) until a pure clone of said previously unculturable microorganism is obtained.

According to the invention, an environmental sample is collected and the number of bacteria is counted/estimated by microscopic observation, namely, all cells are counted in a large square: 12 cells (in practice, several squares are counted and the numbers averaged). The sample is diluted 1/10 in an appropriate medium, 1 ml of the broth is transferred to a tube, diluted again to 1:100, 1 ml thereof is transferred to another tube, and the dilution steps are repeated until about 1:1,000,000, when approximately one bacterium will be entrapped in the gelating agent sphere. The gelating agent sphere is coated with a polymeric membrane and incubated in the environment for weeks to months. At the end of the incubation period, the coated sphere is cut, the bacterium is then isolated, cultured in the sphere, and subjected to molecular biology techniques.

The environmental source from which the samples are collected may be any terrestrial, aquatic or marine source such as soil, biofilms, sediments (e.g. coral or other marine sediments, aquifer sediments and the like), waste waters and the like. The sample is suspended in its natural or other appropriate medium, and is divided, for example, into 1-ml tubes, and each divisional sample is then subjected to counting/estimation of the number of microorganisms by well-known techniques, for example by DAPI (4',6-diamidino-2-phenylindole) staining of the cells and direct microscopic count of the DAPI-stained cells.

In the next step, the samples are diluted as necessary in an appropriate medium. As used herein, an "appropriate medium" is intended to mean a medium compatible with the environment from which the sample has been collected with respect to physico-chemical parameters such as pH, salinity, temperature, oxygen concentration, and the like. The medium may be sterile water, sterile saline, sterile water containing suitable ingredients for compatibility with the environmental source, and the like. For example, a sample collected from a marine source will have the salinity corresponding to the marine source and the salt concentration will be higher if the sample is originated from the Dead Sea. When the sample is collected from soil, the medium may be sterile water.

The next step consists in the addition of a gelating agent as a matrix to the diluted samples. Any suitable natural, semi-synthetic or synthetic gelating agent may be used such as, but not limited to, agar, alginate, carrageenans, gum Arabic, guar gum, traganth gum, xanthan gum, propyleneglycolalginate, and mycrocrystalline cellulose.

In one preferred embodiment, the gelating agent is agar. Preferably, the diluted samples are mixed with warm (40-50° C.) autoclaved agar (0.7-2%) such as to entrap preferably one, or more, microorganisms within a sphere of the gelating agent. The agar spheres can be obtained by dripping agar droplets into cold mineral oil. The sphere size of 0.1 mm or less, up to 5 mm, preferably up to 2-3 mm, in diameter, can be determined by the nozzle diameter and dripping rate.

The gelating agent spheres containing the entrapped microorganism(s) are then coated with a natural or synthetic polymer such as, but not limited to, a polysulfone, an alginate, an epoxy resin, polyacrylamide, silica gel and the like, such as to form a multilayered membrane. Polysulfone resin of average m.w. 35000, Na-alginate, and epoxy resin such as Epikote 255 have been disclosed before for biomass entrapment for different applications (Ferguson et al., 1989; Blanco et al., 1999) and can be used according to the invention.

For coating, the polymer is first dissolved in a suitable solvent, the dried gelating agent spheres containing the entrapped microorganism are introduced into the polymer solution, and are then transferred into a medium that enables coating of the spheres by several layers of the polymer, thus forming the desired spheres coated by the polymeric membrane. In one embodiment, agar spheres containing one or more microorganisms are immersed into a solution of polysulfone in dimethylformamide (DMF) and transferred to water in order to obtain the desired polymeric coating. The polymeric membrane allows exchange of chemicals between the sphere and the environment, but restrict movement of cells. The polymer can be opaque, but preferably it is transparent such that the colonies inside the sphere can be seen.

The next step consists in the incubation of the polymeric coated gelating agent spheres containing one or more microorganisms in the environment from which the original sample has been collected, for an appropriate time. This is the alternative to cultivate such microorganisms that cannot grow in known growth media for microorganisms. The incubation in the environment can take from days to months. When the sample is collected from a marine source, the incubation may be carried out in a container, e.g., aquarium, containing water with the degree of salinity of the marine source. When the sample is collected from soil, the incubation may be carried out in containers, e.g. pots, filled with the same soil material.

After the incubation, the spheres are cut and placed on a glass slide and covered with a coverslip, and the entire volume of agar is scanned for microbial colonies at magnification of 400× and 1,000×. The microorganisms are then isolated into pure culture by successive re-inoculation of individual colonies into new spheres followed by incubation in the environment, by repetition of steps (iii) to (vii) as many times as necessary, until a pure clone of the previously uncultivable microorganism is obtained.

After incubation in the environment, previously uncultured microorganisms can be isolated and then subjected to molecular biology and genomics techniques, and/or cultured for the production of bioactive materials. Libraries can be construed composed of microorganisms, each isolated from a separate sphere, and can be used for identification of new biologically active compounds, even without identification and characterization of the microorganisms. When the identified biologically active compound is a small organic molecule, its structure can be determined by known methods, it is then synthesized, the biological activity is ascertained and it can then be formulated in pharmaceutical or veterinary compositions.

The method of the present invention allows isolation/identification of new types of microorganisms, such as bacteria, previously considered as uncultivable, and the establishment of libraries of "uncultivable" microorganisms useful for the drug discovery and biotechnology industries. The method enables exploration of new natural products from previously uncultured microorganisms New genes might be obtained from the previously uncultivable microbial communities, and new biologically active materials such as proteins, enzymes and antibiotics of utility to humans may be discovered.

According to the invention, metagenomics techniques can be used to address the genetic structure and functional composition of a sample irrespective of whether the microorganism can be cultured. Molecular methodologies such as PCR of select molecular targets can be used to discover genes with useful properties. Microbial communities can be profiled by techniques well known in the art. Cloning and sequencing of molecular targets such as 16S rDNA enable identification of indigenous and novel organisms.

In one embodiment of the invention, cells or extracts from uncultivable microorganisms are subjected to analysis by 16S RNA gene sequencing. Ribosomal RNA genes from the samples, microcolonies or cultures are amplified by PCR by using specific 16S RNA oligonucleotide primers for bacteria. After cloning the PCR products, the inserts are screened by their restriction patterns (RFLP—restriction fragment length polymorphism). The clones are submitted to sequence analysis and compared with known 16S RNA genes using, for example, the online GenBank database (http://ncbi.nlm.nih.gov/GenBank). In this way, it can be determined whether or not the microorganism represents a new species/genus.

The present invention further provides a method for genomic characterization of previously uncultivable microorganisms, which comprises: (i) collecting a sample from an environmental source; (ii) counting/estimating the number of microorganisms in the sample; (iii) diluting the sample in an appropriate medium; (iv) adding a gelating agent such as to entrap one or more microorganisms within a sphere of the gelating agent; (v) coating the spheres containing the entrapped microorganism(s) with a natural or synthetic polymer to form a polymeric membrane; (vi) incubating the coated spheres in the original environment for an appropriate time; (vii) cutting the spheres and extracting the microorganisms by chemical lysis using an agent for extraction of genomic DNA; (viii) processing the total genomic DNA to establish the restriction fragment length polymorphism (RFLP) pattern of the microorganisms; (ix) analyzing the RFLP patterns to identify unique clones that are submitted to sequence analysis; and (x) identifying the microorganisms by comparison of these sequences with sequences available at the GenBank database.

In one preferred embodiment, a method is provided wherein the microorganisms are isolated from a marine source, which comprises: (i) collecting a sample from a marine source; (ii) counting/estimating the number of microorganisms in the sample; (iii) diluting the sample in sterile seawater; (iv) adding a gelating agent such as to entrap one or more microorganisms within a sphere of the gelating agent; (v) coating the spheres containing the entrapped microorganism(s) with a natural or synthetic polymer to form a polymeric membrane; (vi) incubating the coated spheres in an aquarium containing seawater for an appropriate time; (vii) cutting the spheres and extracting the microorganisms by chemical lysis using an agent for extraction of genomic DNA; (viii) processing the total genomic DNA to establish the restriction fragment length polymorphism (RFLP) pattern of the microorganisms; (ix) analyzing the RFLP patterns to identify unique clones that are submitted to sequence analysis; and (x) identifying the microorganisms by comparison of these sequences with sequences available at the GenBank database.

In a preferred embodiment of the present invention, the microorganism is a bacterium isolated from a marine source consisting of coral mucus. According to this embodiment, extracts from uncultivable microorganisms from Red Sea coral mucus were amplified by PCR using the specific 16S RNA oligonucleotide primers for bacteria of SEQ ID NO:1 (forward primer, 8F) and SEQ ID NO:2 (reverse primer, 1512 R).

The most abundant sequence (70%) in this Red Sea coral mucus sample corresponded to the partial 16S rDNA sequence characterized by the SEQ ID NO: 3 (1,428 bp), and represent the Bacteria (domain), Proteobacteria (phylum), Betaproteobacteria (class), Burkholderiales (order), Alcaligenaceae (family), *Alcaligenes* (genus).

The next most abundant clone (20%) in the Red Sea coral mucus sample corresponded to the partial 16S rDNA sequence characterized by the SEQ ID NO:4 (1,382 bp), and represent the Bacteria (domain), Proteobacteria (phylum), Alphaproteobacteria (class), Rhodobacteriales (order), Rhodobacteraceae (family), *Roseobacter* (genus) or *Ruegeria* (genus) or unclassified (genus).

The less abundant clone (10%) in the Red Sea coral mucus sample corresponded to the partial 16S rDNA sequence characterized by the SEQ ID NO: 5 (1,483 bp), and represent the Bacteria (domain), Proteobacteria (phylum), Gammaproteobacteria (class), Endobacteriales (order) or Verrucomicrobiales (order).

In another embodiment of the present invention, the microorganism is isolated from a soil sample. According to this embodiment, a clone from a library constructed from uncul turable soil bacteria from the soil of the Halutza region, Negev, Israel, was amplified by PCR using the specific 16S RNA oligonucleotide primers for bacteria of SEQ ID NO:1 (forward primer, 8F) and SEQ ID NO:2 (reverse primer, 1512 R).

The most abundant clone in the Halutza soil bacteria corresponded to the partial 16S rDNA sequences characterized by the SEQ ID NO: 6 (730 bases, by direct 8F primer) and SEQ ID NO: 7 (689 bases, by reverse 1512R primer) and represent the Proteobacteria (phylum), Betaproteobacteria (class), Burkholderiales (order), Alcaligenaceae (family), *Alcaligenes* (genus).

The next most abundant clone in this sample of Halutza soil bacteria corresponded to the partial 16S rDNA sequences characterized by the SEQ ID NO:8 (651 bases, by direct 8F primer) and SEQ ID NO: 9 (886 bases, by reverse 1512R primer) and represent the Proteobacteria (phylum), Gammaproteobacteria (class), Pseudomonadales (order), Pseudomonadaceae (family), *Pseudomonas* (genus).

In another aspect, the present invention relates to a previously uncultured microorganism isolated by the method of the present invention. The microorganism may be a eukaryote, e.g. a fungus, or a prokaryote, e.g., a bacterium. In a preferred embodiment, the microorganism is a bacterium. In most preferred embodiments, the bacterium is the bacterium isolated from soil depicted in FIG. 3, or it is a bacterium comprising the partial 16S rDNA nucleic acid sequences selected from the group consisting of SEQ ID NO:3, SEQ ID NO:4, and SEQ ID NO:5, or the pair of 16S rDNA sequences consisting of SEQ ID NO:6 and NO:7, or SEQ ID NO:8 and NO:9.

In a further aspect, the present invention relates to a library of previously uncultured microorganisms obtained by the method of the invention and to the use of said library for the discovery of new biologically active agents including, but not being limited, to new antibiotics, enzymes, biocatalysts, genes.

It is further envisaged to construct bacterial artificial chromosome [BAC], cosmid and small insert libraries from diverse environmental samples and then subject the libraries to a screening for novel genes, proteins and small molecules exhibiting activities of interest. For example, 16S rRNA gene clone libraries can be formed from mixed colonies of microorganisms and screened.

The colonies of microorganisms can also be screened for antibiotic activity by contacting diluted samples with a strain of interest and studying the influence on its growth. Colonies of unculturable microorganisms that produce compounds with antibiotic activity will inhibit growth of strains. Said compounds can then be isolated, purified, analyzed and either synthesized for use as antibiotic or used as a model for further drug discovery.

Libraries of test extracts of the microorganisms can also be tested for activity by automated highthrouput biochemical or biological assays using, for example, a panel of test microorganisms to test antibiotic activity, or a panel of enzymes or antibodies to find compounds that affect their activities.

The invention will now be illustrated by the following non-limiting Examples.

EXAMPLES

Example 1

Laboratory Scale Wastewater Bioreactor

An environmental sample was obtained from laboratory scale wastewater bioreactor (waste water from Ramat Hovav Toxic Waste Dumping Site, Negev, Israel) and estimated for microorganism number by DAPI-staining and microscope direct counting ($10^8$-$10^9$ cell/mL). The sample was diluted 8- and 9-fold with water in order to entrap approximately one microorganism in one agar sphere.

The diluted samples were mixed with warm (50° C.) autoclaved agar (DIFCO) (900 µl agar per 100 µl diluted sample, final concentration 1.5% agar). Agar spheres of approximately 1-2 mm in diameter containing the entrapped microorganism(s) were formed by dripping droplets of the mixture into cold mineral oil.

Figure 2:
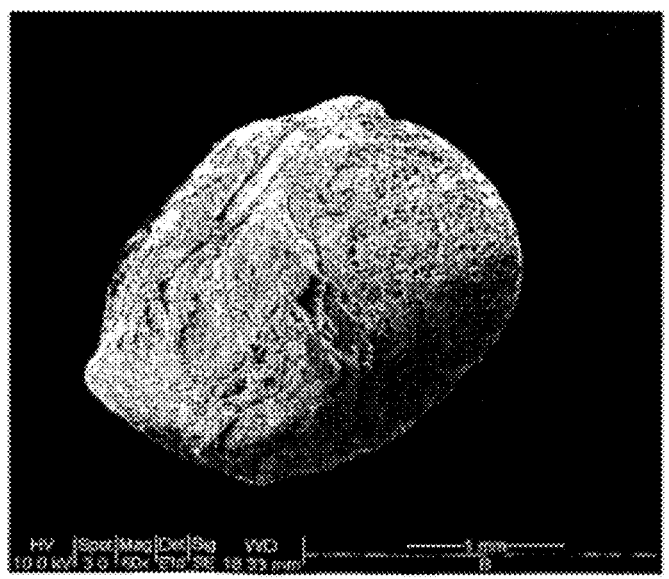
FIG. 2 is a scanning electron micrograph showing an agar sphere coated with a polysulfone membrane as obtained in Example 1 hereinafter.

A solution of 10% polysulfone of m.w. ca. 35,000 (Sigma-Aldrich, Product No. 42,830-2) in DMF was prepared and used to coat the dried agar spheres containing the entrapped microorganism(s). For this purpose, the agar spheres were introduced into the polymer solution, and then transferred into water in order to obtain the desired polymeric membrane. FIG. 2 is a photograph of such a coated agar sphere.

The polysulfone-coated agar spheres containing the entrapped microorganism(s) were then incubated for 3 weeks in a wastewater bioreactor. At the end of the incubation, the agar spheres were cut and placed between a glass slide and a coverslip, and the entire volume of agar was scanned for microbial colonies at magnification of 400× and 1000×.

In the spheres, we could see development of isolated colonies of bacteria and fungi presumably uncultivable, since experiments to grow them in ordinary agar plates were not successful and no bacterial growth was observed.

Example 2

Microbial Communities Inhabiting Coral Mucus

Mucus of coral heads from the Red Sea was sampled by collecting ca. 1 ml$^{-1}$ in a sterile disposable 50-ml polypropylene centrifuge tube. Mucus bacteria were counted directly under phase microscopy. Mucus was diluted by sterile seawater and placed on marine agar for culturable colony forming units (CFU). Several dilutions ($10^{-7}$, $10^{-6}$, $10^{-5}$ and $10^{-4}$) were mixed with 2% marine agar in ratio 1 to 1 and agar spheres were coated with polysulphone and incubated in a seawater aquarium containing corals for several weeks. Agar spheres of approximately 1-2 mm in diameter containing the entrapped microorganism(s) were formed by dripping droplets of the mixture into cold mineral oil.

A solution of 10% polysulfone of m.w. ca. 35,000 (Sigma-Aldrich, Product No. 42,830-2) in DMF was prepared and used to coat the dried agar spheres containing the entrapped microorganism(s). For this purpose, the agar spheres were introduced into the polymer solution, and then transferred into water in order to obtain the desired polymeric membrane.

The polysulfone-coated agar spheres containing the entrapped microorganism(s) were then incubated for 3 weeks in a seawater aquarium containing corals. At the end of the incubation, the agar spheres were cut and placed between a glass slide and a coverslip, and the entire volume of agar was scanned for microbial colonies at magnification of 400× and 1000×.

In the spheres, we could see development of isolated colonies of bacteria presumably uncultivable, since experiments to grow them in ordinary agar plates were not successful and no bacterial growth was observed.

Agar spheres including unculturable bacteria were extracted by chemical lysis protocol using CTAB solution (hexadecyltrimethylammonium bromide, Sigma H-5882) for genomic DNA. The total DNA was amplified with a Mastercycler gradient thermocycler (Eppendorf, Westbury, N.Y.) by PCR using specific 16S rRNA primers for bacteria [forward primer, 8F (5'-GGATCCAGACTTT GAT(C/T)(A/C)TG-GCTCAG—SEQ ID NO:1) and reverse primer, 1512R (5' GTGAAGCTTA CGG(C/T)TAGCTTGTTACGACTT—SEQ ID NO:2)]. Primers used in the PCR amplifications were obtained from Sigma-Genosys. Reaction mixtures included a 12.5 µl ReddyMix (PCR Master mix containing 1.5 mM MgCl$_2$ and 0.2 mM concentration of each deoxynucleoside triphosphate) (ABgene, Surrey, UK), a 1 pmol each of the forward and reverse primers, 1 µl of the sample preparation, and water to bring the total volume to 25 µl. An initial denaturation-hot start of 4 min at 95° C. was followed by 30 cycles of the following incubation pattern: 94° C. for 20 sec, 56° C. for 20 sec, and 72° C. for 105 sec. A final soak at 72° C. for 20 min concluded the reaction.

PCR products were purified by electrophoresis through a 0.8% agarose gel (Sigma), stained with ethidium bromide, and visualized on a UV transilluminator. The approximately 1,500-bp heterologous ribosomal DNA (rDNA) product was excised from the gel, and the DNA was purified from the gel slice by using the QIAquick gel extraction kit (Qiagen, Germany). The gel-purified PCR product was cloned into the pDrive vector by QIAgen PCR cloning kit (Qiagen, Germany) and transformed into calcium chloride-competent XL MRF' *E. coli* cells. Plasmid DNA was isolated from individual clones by QIAprep Spin Miniprep kit (Qiagen, Germany).

Aliquots from a subset of the samples of purified plasmid DNA were digested with 5 U of the restriction enzyme EcoRI for more than 4 h at 37° C., and the digested product was separated by electrophoresis on a 1% agarose gel. After staining with ethidium bromide, the bands were visualized on a UV transilluminator and the RFLP (restriction fragment length polymorphism) patterns were analyzed to select clones containing the appropriately sized insert. Plasmid DNA from these clones was then digested with the six-base recognition site enzymes SphI, SalI, EcoRV, BamHI, HindIII, NotI, XbaI and XhoI (Sigma) under the conditions described above. The digest products were then separated by electrophoresis on a 1% agarose gel, stained with ethidium bromide, and the RFLP patterns were used to identify unique clones to be submitted for sequence analysis.

Three additional internal primers were designed for completed sequencing of the clones. Sequence reactions were performed on the plasmid templates by using an ABI 3700 capillary sequencer. The rDNA sequences were first compared with those in the GenBank database with the basic local alignment search tool (BLAST) network service through San-Diego Supercomputer Center (SDSC). From the alignments created by this search, the orientation of each cloned 16S rRNA gene could be determined and a rough phylogenetic association was established. Each sequence was analyzed using the CHIMERA CHECK program (version 2.7) available at the Ribosomal Database Project.

Clone library constructed from agar spheres (10 colonies) inoculated by mucus, revealed three different patterns by RFLP by ratio 7 to 2 to 1. Representative DNA from each group was partial sequenced by using direct (8F) and reversed (1512R) primers. Microorganism identification was based on comparison of these sequences with the GenBank database and exhibited high division-level diversity of bacterial sequences.

The most abundant clone (70%) is characterized by partial 16S rDNA sequence of SEQ ID NO:3 that represents Bacteria (domain), Proteobacteria (phylum), Betaproteobacteria (class), Burkholderiales (order), Alcaligenaceae (family), *Alcaligenes* (genus). The next most abundant clone (20%) is characterized by partial 16S rDNA sequence of SEQ ID NO:4 that represents Bacteria (domain), Proteobacteria (phylum), Alphaproteobacteria (class), Rhodobacteriales (order), Rhodobacteraceae (family), *Roseobacter* (genus) or *Ruegeria* (genus) or unclassified (genus). The less abundant clone (10%) in the Red Sea coral mucus sample is characterized by partial 16S rDNA sequence of SEQ ID NO:5 that represents Bacteria (domain), Proteobacteria (phylum), Gammaproteobacteria (class), Endobacteriales (order) or Verrucomicrobiales (order).

Example 3

Microbial Communities Inhabiting Soil

A sample was collected from the soil of the Halutza region, Negev, Israel, and processed as described in Example 2. The medium was sterile tapwater and the incubation of the polysulfone-coated agar spheres was carried out in pots filled with soil material from the Halutza region. A clone library constructed from agar spheres (10 colonies) inoculated with the soil bacteria was incubated for 3 weeks, analyzed as described above and revealed two different patterns by RFLP by ratio 9 to 1. DNA from two clones were partially sequenced by using direct (8F) and reversed (1512R) primers and microorganism identification was based on comparison of these sequences with the GenBank database.

The most abundant sequence (90%) of this sample of soil bacteria is characterized by partial 16S rDNA sequences of SEQ ID NO:9 and SEQ ID NO:10, that represent Proteobacteria (phylum), Betaproteobacteria (class), Burkholderiales (order), Alcaligenaceae (family), *Alcaligenes* (genus). The less abundant (10%) clone is characterized by partial 16S rDNA sequences of SEQ ID NO:11 and SEQ ID NO:12, that represent Proteobacteria (phylum), Gammaproteobacteria (class), Pseudomonadales (order), Pseudomonadaceae (family), *Pseudomonas* (genus).

Figure 3:
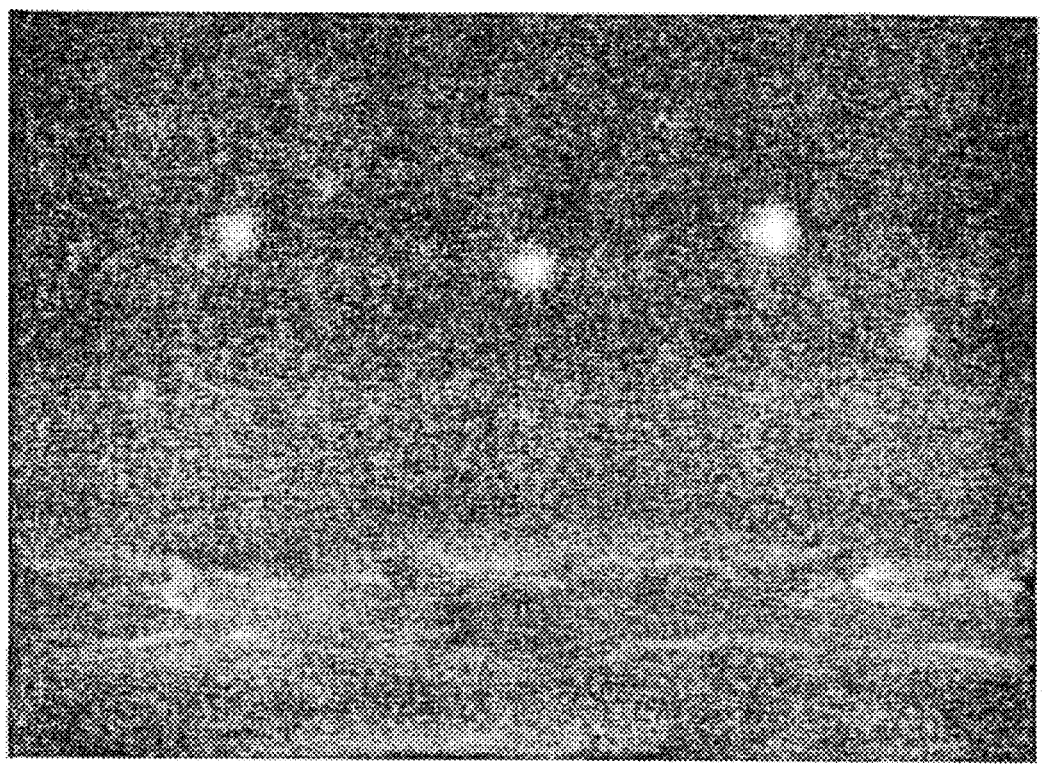
FIG. 3 is a photograph (×1000) of microcolony of an unidentified rod-shaped bacterium obtained from soil as described in Example 3 hereinafter.

FIG. 3 is a photograph (×1000) of a microcolony of an unidentified rod-shaped bacterium obtained in purified form from the Halutza soil.

REFERENCES

Amann, R. I., Ludwig, W. and Schleifer, K-H. (1995) Phylogenetic identification and in situ detection of individual microbial cells without cultivation. Microbiol. Rev. 59,143-169.

Blanco A., Sanz B., Llama J. M., Serra L. M. (1999). Biosorption of heavy metals to immobilised Phormidium laminosum biomass. Journal of Biotechnology 69: 227-240.

Felske A., Wolterink A., van Lis R., W. M. de Vos, A. D. L. Akkermans. (2000). Searching for predominant soil bacteria: 16S rDNA cloning versus strain cultivation. FEMS Microbiology Ecology 30:137-145.

Ferguson C. R., Peterson M. R., Jeffers T. H. (1989). Removal of metal contaminants from waste waters using biomass immobilized in polysulfone beads. In: Scheiner, B. J., Doyle, F. M., Kawatras, S. K. (Eds.), Biotechnology in Minerals and Metal Processing. Society of Mining Engineers, Littleton, Colo., pp. 193-199.

Handelsman J., Rondo R. M., Brady F. S., Clardy J., Goodman M. R. (1998). Molecular biological access to the chemistry of unknown soil microbes: a new frontier for natural products. Chem. Biol. 5(10):245-249.

Head I. M., Saunders J. R., Pickup R. W. (1998). Microbial Evolution, Diversity, and Ecology: A Decade of Ribosomal RNA Analysis of Uncultivated Microorganisms. Microb Ecol 35:1-21.

Kaeberlein T., Lewis K., Epstein S. (2002). Isolating "uncultivable" microorganisms in pure culture in a simulated natural environment. Science 296: 1127-1129.

Spring S., Schulze R., Overmann J., Schleifer K. (2000). Identification and characterization of ecologically significant prokaryotes in the sediment of freshwater lakes: molecular and cultivation studies. FEMS Microbiology Reviews 24:573-590.

Wintzingerode F., Goebel U., Stackebrandt E. (1997). Determination of microbial diversity in environmental samples: pitfalls of PCR-based rRNA analysis. FEMS Microbiology Reviews 21:213-229.

Zengler K., Toledo G., Rappé M., Elkins J., Mathur J. E., Short J. M., and Keller M. (2002). Cultivating the uncultured. PNAS 99 (24): 15681-15686.

The invention claimed is:

1. A method for isolating and culturing a pure clone of a previously unculturable microorganism, which comprises:
   (i) collecting a sample from an environmental source;
   (ii) counting/estimating the number of microorganisms in said sample;
   (iii) diluting said sample in an appropriate medium;
   (iv) adding a natural gelling agent and entrapping one or more microorganism(s) within a sphere of said gelling agent;
   (v) coating said spheres containing said entrapped microorganisms(s) with a synthetic transparent or opaque polymer selected from the group consisting of a polysulfone, an epoxy resin, a polyacrylamide, and silica gel to form a polymeric membrane;
   (vi) incubating said coated spheres in the original environment for an appropriate time;
   (vii) cutting said spheres and scanning for colonies of microorganisms; and
   (viii) isolating the microorganisms, and repeating steps (iii) to (vii) until a pure clone of said previously unculturable microorganism is obtained.

2. A method according to claim 1, wherein said environmental source is a terrestrial, an aquatic or a marine source.

3. A method according to claim 1, wherein said appropriate medium of (iii) is a medium compatible with the environment from which said sample has been collected.

4. A method according to claim 1, wherein said natural gelling agent of (iv) is selected from the group consisting of agar, alginate, carrageenans, gum arabic, guar gum, tragacanth gum, xanthan gum, propylene glycol alginate, and micro-crystalline cellulose.

5. A method according to claim 1, wherein said sphere of (iv) has a size from 0.1 mm to 5 mm.

6. A method according to claim 1, wherein said gelling agent sphere of (iv) has a size of 1-2 mm in diameter.

7. A method for genomic characterization of previously unculturable microorganism, which comprises:
   (i) culturing a previously unculturable microorganism according to the method of claim 1;
   (ii) cutting said spheres and extracting said microorganism (s) by chemical lysis using an agent for extraction of total genomic DNA;
   (iii) processing said total genomic DNA to establish the restriction fragment length polymorphism (RFLP) pattern of the microorganisms;
   (iv) analyzing said RFLP pattern to identify unique clones that are submitted to sequence analysis; and
   (v) identifying the microorganisms by comparing said sequences with known sequences.

8. A method according to claim 4, wherein said gelling agent is agar.

9. A method according to claim 7, wherein said microorganism(s) are isolated from a marine source.

* * * * *